United States Patent [19]
Westwood

[11] Patent Number: 5,662,625
[45] Date of Patent: Sep. 2, 1997

US005662625A

[54] PRESSURE CONTROLLABLE HYPERBARIC DEVICE

[75] Inventor: Joseph R. Westwood, Glen Mills, Pa.

[73] Assignee: GWR Medical, L.L.P., Chadds Ford, Pa.

[21] Appl. No.: 643,486

[22] Filed: May 6, 1996

[51] Int. Cl.[6] .................. A61F 13/00; A61G 10/00
[52] U.S. Cl. .................. 604/305; 604/307; 604/23; 128/202.12
[58] Field of Search .................. 604/304–307, 604/23; 128/202.12, 202.13

[56] References Cited

U.S. PATENT DOCUMENTS

| | | | |
|---|---|---|---|
| 3,026,874 | 3/1962 | Stevens | 604/305 |
| 3,744,491 | 7/1973 | Fisher | 128/184 |
| 3,874,387 | 4/1975 | Barbieri | 604/307 |
| 4,003,371 | 1/1977 | Fisher | 128/184 |
| 4,224,941 | 9/1980 | Stivala | 128/207.26 |
| 4,474,571 | 10/1984 | Lasley | 128/202.12 |
| 4,772,259 | 9/1988 | Frech | 604/23 |
| 4,911,699 | 3/1990 | Fenton | 604/333 |
| 5,000,164 | 3/1991 | Cooper | 128/202.12 |
| 5,029,579 | 7/1991 | Trammell | 128/205.26 |
| 5,154,697 | 10/1992 | Loori | 604/23 |
| 5,256,159 | 10/1993 | Newman | 604/317 |
| 5,411,496 | 5/1995 | Homa | 604/333 |
| 5,441,491 | 8/1995 | Verschoor et al. | 604/304 |
| 5,478,310 | 12/1995 | Dyson-Cantwell et al. | 604/23 |

OTHER PUBLICATIONS

Heng et al., "A Simplified Hyperbaric Oxygen Technique for Leg Ulcers", Arch Dermatol, pp. 640–645. May 1984.

*Primary Examiner*—Robert A. Clarke
*Assistant Examiner*—David J. Cho
*Attorney, Agent, or Firm*—Robert J. Reichert

[57] ABSTRACT

A method of treating a wound with therapeutic gas to expedite healing, and a topical hyperbaric device to carry out the method having a maximum pressure release valve that can be set a desired maximum treatment pressure and that is not connected to the gas supply.

2 Claims, 1 Drawing Sheet

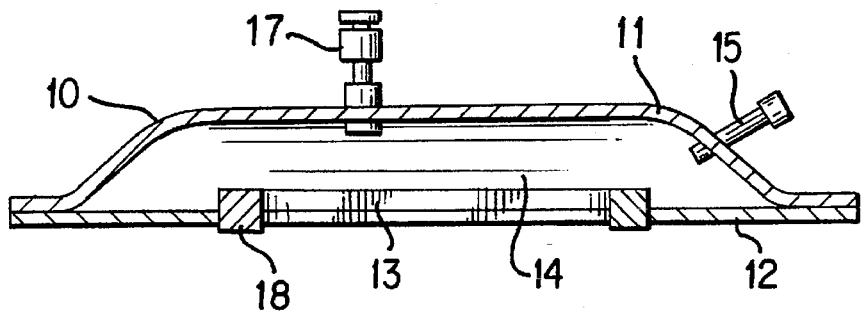
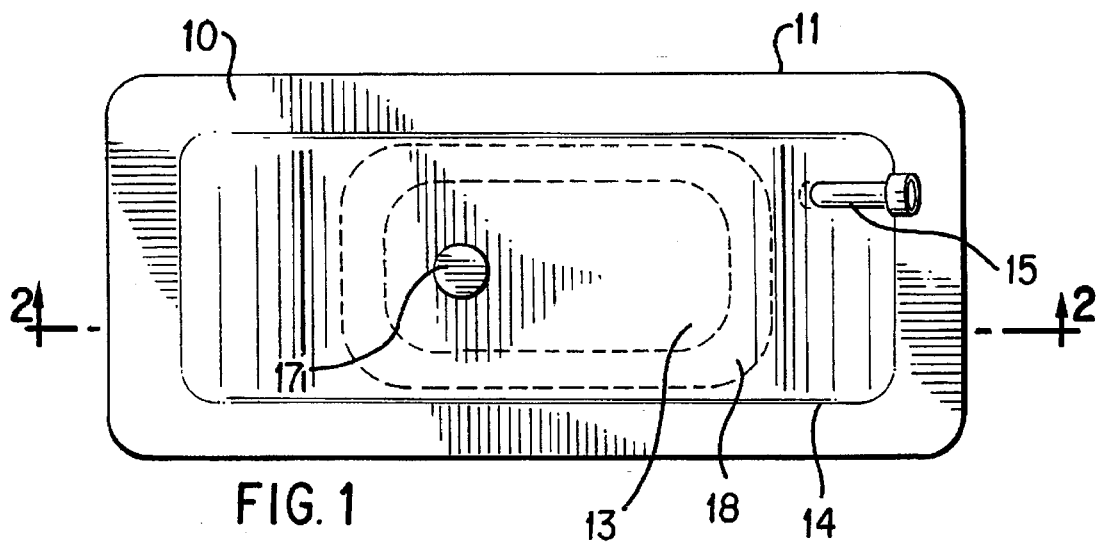
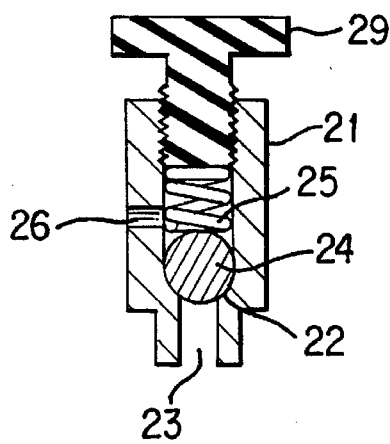
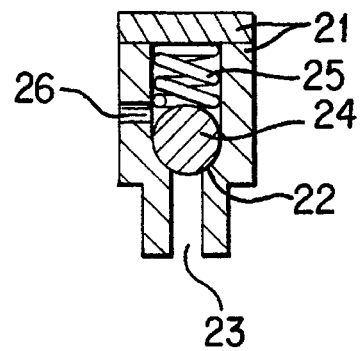

PRESSURE CONTROLLABLE HYPERBARIC DEVICE

BACKGROUND OF THE INVENTION

Many difficult to heal wounds, particularly where there is damage to the blood circulation system, are now treated with a gas such as oxygen to supplement the oxygen to the wound area that is not being satisfied by the damaged blood circulation system. Initially, this was done by installing a gas chamber around the wound and flowing oxygen continuously over the wound area. These chambers were rigid, heavy, difficult to clean between uses, and uncomfortable for the patient. Recently it has been discovered that continuous flow of oxygen is not necessary, and that effective hyperbaric treatment can be obtained by using a single adequate stationary charge of oxygen that is retained in a flexible chamber in contact with the wound for the treatment period. Unlike the continuous flow type devices, these devices do not need to be continuously attached to the oxygen supply during treatment, allowing mobility for the patient.

Many flexible topical hyperbaric bags are known. U.S. Pat. No. 5,154,697 assigned to Topox, Inc. discloses a hyperbaric bag that has a hole through the side of the bag that is to be exposed to the area to be treated. The periphery of the hole is reinforced with a strong ring. A belt structure affixes the bag over the area to be treated, and gas such as oxygen inflates the bag to the desired gas pressure. The device contains a gas inlet for charging and a gas pressure release valve which is constructed for a fixed single maximum gas pressure. Unlike earlier hyperbaric devices, the device of this patent does not require a constant supply of gas. Although it is known that there are different narrow optimum pressures ranges for treating arterial wounds and venous wounds, the Topox bag is not designed to operate at a specific prescribed pressure. The devices cannot be adjusted to an optimum pressure in response to a wound diagnosis.

Dyson-Cantwell U.S. Pat. No. 5,478,310 discloses a hyperbaric oxygen chamber for use on leg wounds. It comprises a polyethylene bag to be secured around the leg and ages supply line. This device does have a pressure control means but it is connected to the gas supply line. As shown in FIG. 3, the chamber may have a tape covering holes in the gas bag that can be pulled off the holes during treatment to decrease gas pressure. Using this device it is difficult, if at all possible, to set and maintain the treatment pressure within the range of desired treatment pressure.

The prior art also discloses numerous topical hyperbaric devices that apply a continuous supply of gas flowing through the wound area. These of course require continuous connection to the gas supply, eliminating patient mobility during treatment.

Some of these prior art continuous flow devices have pressure control valves that are connected to and control the gas input See Stivala U.S. Pat. No. 4,224,921; Tramell U.S. Pat. No. 5,029,479; and Frech U.S. Pat. No. 4,772,259.

Pressure control means connected to the gas supply have several disadvantages. When the gas supply is disconnected or shut off the pressure control means is disconnected or shut off; and so the pressure control means is no longer functional. This is particularly important for devices designed for static treatment use. Also, accurate control of the treatment zone pressure is difficult because such valves are not directly measuring the treatment zone pressure. Furthermore, putting a pressure control valve in the gas supply line requires using an additional device, in addition to the gas cylinder or hospital gas supply line. In such a device the gas supply line cannot be directly connected to the hyperbaric treatment device treatment zone.

SUMMARY OF THE INVENTION

The present invention relates to a method of treating a patient's wound with a therapeutic gas to expedite healing, and hyperbaric treatment devices for practicing this method.

The method of the present invention comprises: diagnosing the wound to determine a treatment zone desired maximum gas pressure; selecting a hyperbaric treatment device capable of receiving the therapeutic gas from a gas supply, which device has a means not in direct communication with the gas supply to set the maximum treatment zone gas pressure; setting this means at the desired maximum gas pressure; affixing the device encompassing the wound to make a treatment zone including the wound, within which zone the gas is restricted; and introducing sufficient therapeutic gas into the treatment zone to substantially maintain the gas pressure therein at the desired maximum pressure. This treatment is continued for the prescribed duration and repeated at the prescribed intervals, determined by the diagnosis. Preferably the treatment is a static charge treatment, wherein the gas is retained in the treatment zone for a prolonged period of time so that the gas supply can be disconnected giving patient comfort.

The topical hyperbaric devices of the present invention are ideally suited to carry out the method of this invention. This device comprises a flexible substantially gas impermeable sheet of material that is capable of confining the therapeutic gas to a restricted therapeutic gas treatment zone; means to affix the material to make a restricted therapeutic gas treatment zone encompassing the wound, wherein the gas is kept in contact with the wound and is restricted from escaping from the treatment zone; means for introducing the therapeutic gas into the treatment zone; and a pressure release valve capable of setting the maximum gas pressure of the treatment zone to the desired treatment pressure, which valve is not in direct communication with the mean for introducing the gas. The valve automatically releases gas from the treatment zone when the maximum pressure is exceeded, which pressure can be pre-set at the desired maximum pressure in the zone. Preferably the valve is manually adjustable so that the desired maximum pressure of the treatment zone can be set accurately at the appropriate gas pressure determined by diagnosis.

BRIEF DESCRIPTION OF THE DRAWINGS

For a detailed description of the preferred embodiments of the topical hyperbaric device of the present invention, reference is made to the drawings in which:

FIG. 1 is a top view of the preferred static hyperbaric device;

FIG. 2 is a cross section of the device of FIG. 1;

FIG. 3 is schematic cross section of a manually adjustable pressure release valve suitable for use in the device of FIG. 1; and FIG. 4 is a schematic cross section of a readily replaceable fixed pressure release valve, also suitable for use in the device of FIG. 1.

DEFINITIONS

The term "gram gas pressure" means the not-to-be exceeded highest gas pressure.

The term "optimum gas pressure" means the most effective therapeutic gas treatment pressure for achieving desired healing.

The term "desired maximum gas pressure" means the highest gas pressure to be used in a particular treatment. It may be the exact pressure prescribed from the diagnosis, or it may be somewhat higher than the prescribed pressure to achieve an average of close to the prescribed pressure during treatment In continuous flow treatment, the "desired maximum gas pressure" normally is the prescribed pressure.

The term "substantially maintain the gas pressure", as used herein in reference to the treatment zone gas pressure, means the gas pressure is maintained close to the desired gas pressure by restricting escape of gas and/or adding gas during treatment. "Substantially" means to include deviation from the precise desired maximum gas pressure; this deviation may be as much as 30% or more so long as the deviation is not too much for adequate treatment in the particular case.

The term "retained", as used herein with respect to gas in the treatment zone, means the gas is kept in the treatment zone (static treatment, not continuous flow treatment). "Substantially retained" refers to the normal situation in static treatment wherein some gas leakage is expected, possibly requiring period replenishment.

The term "restricted", as used in reference to the treatment zone gas, means excessive uncontrolled escape of gas from the treatment zone is prevented. In static treatment, optimally "restricted" and "retained" mean completely prevented from escaping. Of course this level of restriction is seldom, if ever achieved, and so the term "restricted" is intended to include substantial gas escape so long as adequate therapeutic gas is maintained in the treatment zone. "Restricted" also applies to continuous flow treatment, where gas is continuously fed and exited from the treatment in a controlled manner while maintaining treatment zone pressure; uncontrolled escape of gas is minimized.

The term "substantially gas impermeable", as used herein with respect to the sheet material, means gas impermeable to the extend needed to prevent excessive gas escape from the treatment zone through the sheet material. Total gas impermeability seldom is needed, particularly for continuous flow treatment devices. However, generally high impermeability is desirable for static treatment devices.

The term "continuous flow treatment" means treatment during which gas is substantially continuously added and exited through most of the treatment period. It may include periods when the gas supply pressure is decreased, allowing treatment at a lower pressure, but the gas supply remains connected.

The term "static treatment" means treatment during which an initial charge of gas is retained in the treatment zone for a prolonged treatment time period, and there is no continuous flow of gas to the treatment zone during treatment. In static treatment, intermittent gas additions may be needed during the treatment period to replace escaped gas and maintain gas pressure.

DETAILED DESCRIPTION OF THE PREFERRED EMBODIMENTS

To practice the method of the present invention, before treatment the wound is diagnosed to determine whether arterial or venous and the desired maximum treatment gas pressure, duration and sequence of treatments. Normally, if the wound is arterial an optimum treatment pressure in the range of about 25-35 mm Hg, and if venous a desired pressure in the range of about 15-20 mm Hg, is therapeutically optimal. Typically a 7 day treatment period is prescribed comprising identical one to two hour treatments on days 1, 2, 3 and 4, followed by no treatment on days 5 thru 7, which treatment usually is repeated one or more times.

An appropriate topical hyperbaric device capable of receiving gas from a gas supply source is then selected. This device comprises a means not in direct communication with the gas supply to accurately set the maximum treatment zone gas pressure at the desired maximum pressure determined by the diagnosis. This desired maximum pressure will be set to give an average treatment pressure, usually within the optimum ranges set forth above. The desired maximum pressure setting is achieved either by selecting a release pressure valve that is fixed at the appropriate desired maximum pressure, or using a hyperbaric treatment device having a manually adjustable maximum pressure valve and manually setting it at the desired maximum pressure.

The topical hyperbaric treatment device is then affixed to the patient to encompass the wound and make a treatment zone including the wound, into which gas is introduced and restricted from escaping. Sufficient therapeutic gas is then introduced into the treatment zone to maintain the gas pressure therein substantially at the desired maximum pressure. If a preferred static pressure device is being used, it will retain a single static gas charge for a prolonged period of time, the duration of which depends on how well the device is able to restrict the gas and retain it in the treatment zone. Some times it is necessary to add gas periodically to substantially maintain the desired maximum pressure. When gas is added, addition is continued until the pressure release valve starts to release gas, indication that the desired maximum pressure in the treatment zone has been reached. The need for additional gas can be noted by observing diminished volume in the treatment zone, i.e. a softening or flattening bag. Alternatively the device may have a pressure gauge connected to the treatment zone.

The present invention product is a flexible pressure controllable topical hyperbaric device for treating wounds and lesions with a therapeutic gas, particularly oxygen. The device comprises a flexible substantially gas impermeable sheet material capable of applying and confining a gas to the therapeutic treatment zone, including the area of the wound to be treated; means to deliver gas to said area; and at least one maximum pressure release valve means that is in direct communication with the treatment zone but is not in direct communication with the gas supply. Preferably a manually adjustable release valve means is used because such a valve means can be set easily and accurately before use to whatever desired maximum gas pressure is prescribed, insuring the correct pressure for the particular treatment. For example, when treating arterial wounds average treatment pressures in the range of 25-35 mm Hg above atmospheric are optimum whereas when treating venial wounds pressures in the range of about 15-20 mm Hg are optimum. A standardized hyperbaric treatment device having a manually adjustable pressure release valve means can be used for whatever desired maximum pressure is prescribed. Desirably the valve means can be set accurately (either by an adjustable valve or by selecting the appropriate fixed pressure release valve element) accurately within the range of about 3 to 60 mm Hg., with an accuracy of about 10 mm Hg., preferably 5 mm Hg.

Referring to FIGS. 1 and 2, a preferred static treatment device 10 of the present invention comprises a sheet of flexible gas impermeable sheet material 11 and 12 that is capable of confining gas and retaining it in a restricted therapeutic gas treatment zone. The confining sheet material has a wound access opening 13, which in use is placed circumferentially over the wound. As shown here, opening 13 is defined by reinforcing ring 18 of strong flexible material capable of fitting to the contour of the wound periphery. Preferably the skin contact side of ring 18 is coated with a layer of adhesive. The wound, around which ring 18 is securely affixed by adhesive or pressure from a belt, and the gas pouch 14 of device 10 define a restricted therapeutic treatment zone encompassing the wound, wherein therapeutic gas is retained in contact with the wound and is restricted from escaping. In this device, gas inlet tube 15 has a one way valve that permits intermittent addition of gas, but not escape thereof. This fitting is adapted to connect directly with the gas supply. Maximum pressure release valve 17 is in direct communication with the treatment zone; it is not in direct communication with the gas supply. As a desirable option, there may be a pressure gauge (nor shown) in communication with gas pouch 14 which shows the treatment zone gas pressure. If so, a single unit comprising the maximum pressure valve and the pressure gauge is preferred, although separate units can be used.

FIG. 3 schematically shows a manually adjustable pressure release valve 17. This is a screw top valve that increases the treatment zone maximum pressure as screw 29 is screwed down. It comprises plastic cylindrical housing 21 that has an internal shoulder 22 at the bottom end with an opening 23 therein. Valve ball 24 seats on shoulder 22 sealing opening 23 closed. Tension spring 25 fits snugly above ball 24 along the inner sides of housing 21, and exerts the selected release pressure on ball 24. Spring 25 is designed to be able to exert about 5–60 mm Hg on ball 25. Screw top 29 is threaded into the top of housing 21 so that it's plunger end abuts the top of spring 25. As screw 26 is screwed in it compresses spring 25, increasing the pressure on ball 24. When the pressure in the treatment zone exceeds the force of spring 25, ball 24 moves upward in the chamber of housing 21, allowing gas to escape from the treatment zone through opening 23 into the chamber of housing 21 and out through exhaust port 26.

Referring to FIG. 4, the pressure release valve need not be adjustable. Instead the valve may be a fixed release pressure female element that is easily inserted or screwed into a male receptacle in communication with the treatment zone. This device also comprises opening 23, ball 24, spring 25 and exhaust port 26 which function the same as there counterparts of FIG. 3. A selection of such fixed pressure release elements is made available, from which an element having the desired maximum release pressure setting is selected. These elements may be color coded to indicate their release pressure. When a fixed pressure release valve is used, the need for a pressure gauge is small.

The design of the pressure release valve is not critical. Many different types are suitable. For example, instead of a ball valve as shown in FIGS. 3 and 4, the release valve can be a baffle valve such as a flap or butterfly baffle valve. Other valves are equally suitable, so long as they are capable of accurately setting the maximum release pressure and are inexpensive and so discardable. If desired the adjustable valve can be calibrated to show the pressure setting. The preferred valve bodies are made of any rigid plastic, although metals such as stainless steel can be used. The spring preferably is steel. Very inexpensive completely plastic valves can be used.

The pressure release valves of FIGS. 3 and 4 are inexpensive yet reliably accurate, within the preferred accuracy ranges. If desired, they can be removed from the hyperbaric treatment device when the device is being cleaned between applications. The entire hyperbaric treatment device, including the valve, is inexpensive and disposable. Using a valve that is in communication with the treatment zone and not with the gas supply eliminates the need for a separate pressure control mechanism between the hyperbaric treatment device and the oxygen source. The hyperbaric device can be connected directly to the gas cylinder or hospital gas supply line.

The material from which the flexible sheet is made can be any strong substantially gas impermeable material. Cast plastic sheeting material, such as polyurethane, polyethylene terephthalate, polyvinyl chloride, or ethylene/polyvinyl copolymer sheet stock, and vapor proof treated fabric such as nylon are suitable. For many uses it is desirable that the sheet material be transparent. The flexible sheet material can have a variety of shapes. It is a rectangular two sided envelope configuration in FIGS. 1 and 2. It can be a single layer, such as a bag to surround a limb. Or it can be a double layer cuff to go around a limb. For wounds on the back or buttocks, the rectangular envelope is best suited.

These devices of FIGS. 1–4 are used in the preferred static treatment method of the present invention to treat wounds that need hyperbaric therapeutic gas treatment, particularly with oxygen. It is known that for optimum treatment "the pressure of oxygen is regulated to be between approximately 25–30 mm Hg for arterial injuries, burns and pyoderma gangrenosum and preferably between 18–20 mm Hg for venous ulcers" (U.S. Pat. No. 5,478,310, Col 3, lines 65 et seq.). The method of the present invention for treating a wound with a therapeutic gas is carried out using the device of FIGS. 1 and 2 by affixing the gas treatment opening over the wound and securely affixing or adhering it to the patient out of contact with the wound. The pressure release valve is set at the prescribed desired treatment pressure determined by diagnosis, normally slightly above the optimum treatment gas pressure. A charge of oxygen is then fed to the device though the gas inlet tube. If the device has a pressure gauge, the gas is introduced until the gas pressure gauge shows a pressure slightly above the desired treatment pressure. The pressure release valve is then turned to adjust the pressure lower until the desired maximum gas pressure level is stabilized. If there is no pressure gauge, the pressure release valve is set at the desired maximum release pressure and gas is introduced until the valve is activated, showing that the treatment zone has been charged to the desired maximum gas pressure. The gas supply then may be disconnected so that the patient has mobility. The device restricts and confines the gas, restraining it within the treatment zone and substantially maintaining pressure at the desired level for a prolonged period of time from the initial gas charge. Nevertheless, as the treatment continues, usually gas will need to be added to replace leaked gas. This is readily done by re-attaching the gas supply and adding gas as necessary.

If a continuous gas flow treatment is prescribed, a continuous treatment hyperbaric device is used. It is similar to the device of FIGS. 1 and 2, except that it also has a gas outlet port or tube. The gas supply remains attached during the treatment, and supplies a flow of gas substantially continuously throughout treatment. The gas flows across the wound and exits out of the treatment zone through the outlet port. The rate of feed of the gas depends on the size of the outlet port, and is sufficient to substantially maintain the desired treatment pressure. More constant treatment zone gas pressure may be attainable using a continuous treatment hyperbaric device.

Although the invention herein has been described with references to particular embodiments, it is to be understood that the embodiments are merely illustrative of the principles and applications of the present invention. It is therefore to be understood that numerous modifications may be made to the embodiments and that other arrangements may be devised without departing from the spirit of the present invention as defined by the claims.

What is claimed:

1. A topical hyperbaric device for treatment of a patient's wound with a therapeutic gas comprising flexible substantially gas impermeable sheet material; and adhesive layer to affix said material to said patient to form a restricted therapeutic gas treatment zone that includes the area of said wound, wherein said gas is in contact with said wound and is restricted from escaping; means for introducing said gas into said treatment zone; and a pressure release valve that automatically releases gas from said treatment zone when the set maximum gas pressure of said valve is exceeded in said treatment zone, characterized by said valve being constructed to be i) manually adjustable, ii) adjustable before therapeutic gas treatment of said wound to an initial desired maximum gas pressure of said treatment zone, and iii) adjustable during uninterrupted therapeutic gas treatment to another desired treatment pressure.

2. The device of claim 1 wherein said treatment zone retains substantially the entire initial charge of said gas in said treatment zone during the treatment period.

* * * * *